(12) United States Patent
Cheetham

(10) Patent No.: US 8,316,702 B2
(45) Date of Patent: Nov. 27, 2012

(54) APPARATUS AND METHOD TO DETERMINE THE ADHESIVE STRENGTH OF MATERIALS

(75) Inventor: Joshua James Cheetham, Windsor (AU)

(73) Assignee: SDI Limited, Brunswick (AU)

( * ) Notice: Subject to any disclaimer, the term of this patent is extended or adjusted under 35 U.S.C. 154(b) by 246 days.

(21) Appl. No.: 12/691,713

(22) Filed: Jan. 21, 2010

(65) Prior Publication Data

US 2010/0186494 A1    Jul. 29, 2010

(51) Int. Cl.
*G01N 19/04* (2006.01)
(52) U.S. Cl. .................................................. 73/150 A
(58) Field of Classification Search .................. None
See application file for complete search history.

(56) References Cited

U.S. PATENT DOCUMENTS

| | | | | |
|---|---|---|---|---|
| 3,683,682 A * | 8/1972 | Jochmann | | 73/842 |
| 5,201,230 A * | 4/1993 | Sakakibara | | 73/827 |
| 6,324,916 B1 * | 12/2001 | Jessop | | 73/842 |
| 7,426,855 B2 * | 9/2008 | Aubele et al. | | 73/150 A |
| 2004/0155381 A1 * | 8/2004 | Clark et al. | | 264/319 |
| 2006/0157891 A1 * | 7/2006 | Hardy et al. | | 264/261 |
| 2007/0141193 A1 * | 6/2007 | Suga | | 425/437 |
| 2010/0307259 A1 * | 12/2010 | Cheetham | | 73/827 |
| 2011/0064871 A1 * | 3/2011 | Uchida et al. | | 427/130 |

* cited by examiner

*Primary Examiner* — Andre Allen
(74) *Attorney, Agent, or Firm* — William H. Holt

(57) ABSTRACT

An apparatus (10) for determining the adhesive strength of materials has a test rig (12) with a base plate (14). A compression plate (20) is provided above a support (18). The compression plate (20) is urged into engagement with the support (18) by means of springs (22). The compression plate (20) has a recess (30) which receives a mould (32). The support (18) contains a substrate (34) which engages with material to be tested contained in the mould (32).

The application also relates to a method which involves measuring the force required to remove the mould (32) from the substrate (34).

11 Claims, 7 Drawing Sheets

APPARATUS AND METHOD TO DETERMINE THE ADHESIVE STRENGTH OF MATERIALS

The present invention relates to an apparatus and method for determining the adhesive strength of materials.

In accordance with one aspect of the present invention there is provided an apparatus for determining the adhesive strength of materials comprising a test rig having a base plate, a compression plate resiliently mounted to the base plate, the compression plate containing a lateral aperture arranged to receive a mould, the compression plate being spaced apart from the base plate so as to enable a substrate to be located between compression plate and the base plate, the compression plate being arranged to be urged into engagement with the mould when the latter is mounted on the substrate.

In accordance with a further aspect of the present invention there is provided a method for determining the adhesive strength of materials which comprises mounting a mould on a substrate, inserting a quantity of material to be tested into the mould, applying pressure to the mould to retain it in position on the substrate, so that the material is in contact with the substrate, and then measuring the force required to remove the mould from the substrate.

The present invention will now be described, by way of example, with reference to the accompanying drawings, in which.

Referring to the Figures, there is shown an apparatus 10 for determining the adhesive strength of materials.

Figure 1:
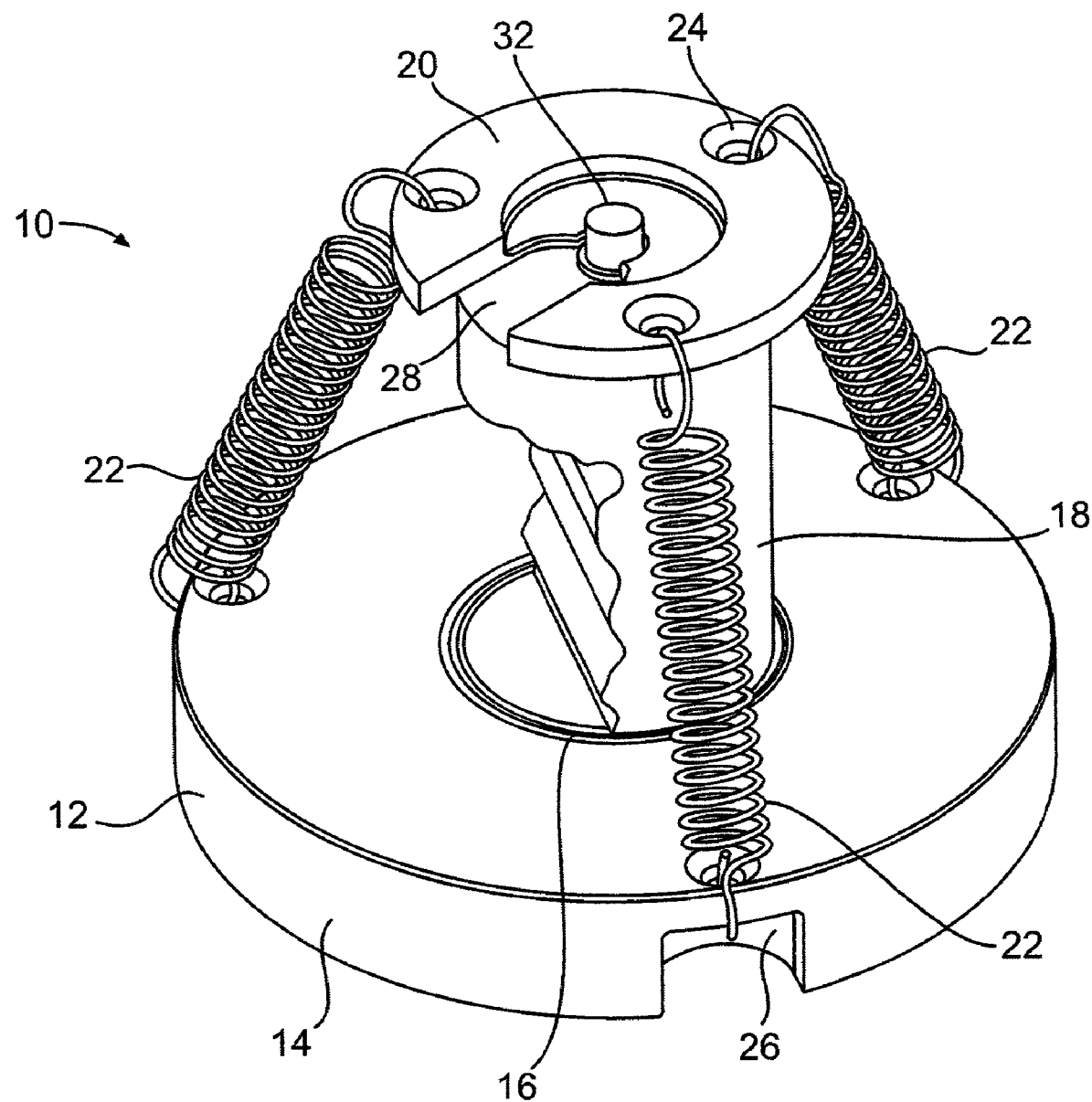
FIG. 1 is a perspective view of a test rig apparatus of the present invention.

As shown in FIG. 1, the apparatus 10 comprises a test rig 12 which has a base plate 14 having a centre surrounded by a plurality of concentric annular recessed rings 16 which are used to locate centrally a cylindrical support as will be described.

A cylindrical support 18 (shown partly broken away) is mounted on the base plate 14 within the rings 16. The support 18 fits snugly within the rings 16 and has an upper surface.

A compression plate 20 is mounted above the support 18. The compression plate 20 is initially disposed to one side of the centre of the plate 14. Further the compression plate 20 is urged downwardly into engagement with the support 18 by means of a plurality of angularly spaced coil springs 22. The springs 22 engage with respective apertures 24 in the compression plate 20 and corresponding recesses 26 in the base plate 14.

As can be seen the compression plate 20 has a lateral aperture 28 which extends inwardly from one side and terminates in a small centrally located recess 30. The recess 30 is arranged to receive and engage with a mould 32.

Figure 2:
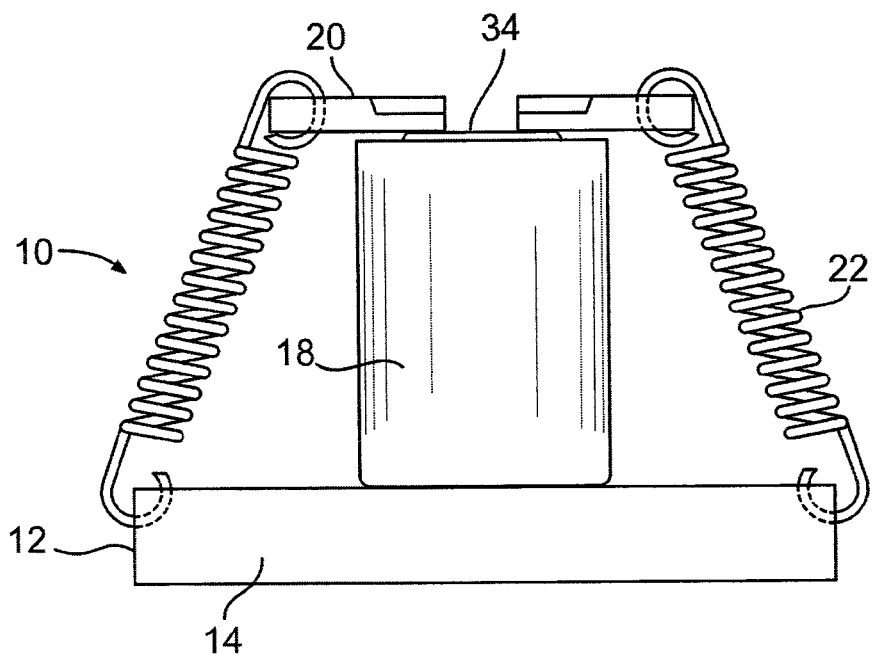
FIG. 2 is a side view of the test rig apparatus of FIG. 1.
Figure 3:
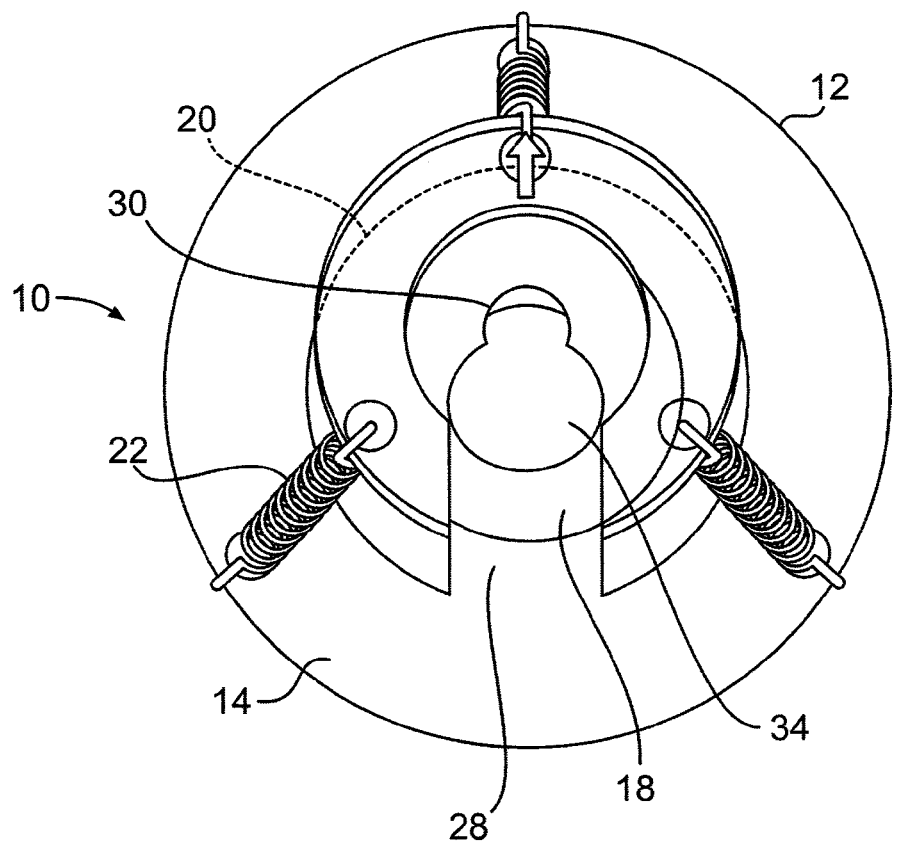
FIG. 3 is a plan view of the test rig apparatus of FIG. 1.

The support 18 contains a centrally axially disposed substrate 34 located within the support 18 (see FIGS. 2 and 3). The substrate 34 could be composed of a tooth material (dentin or enamel surface), a metal, a ceramic, a polymer or another known dental material.

Figure 4:
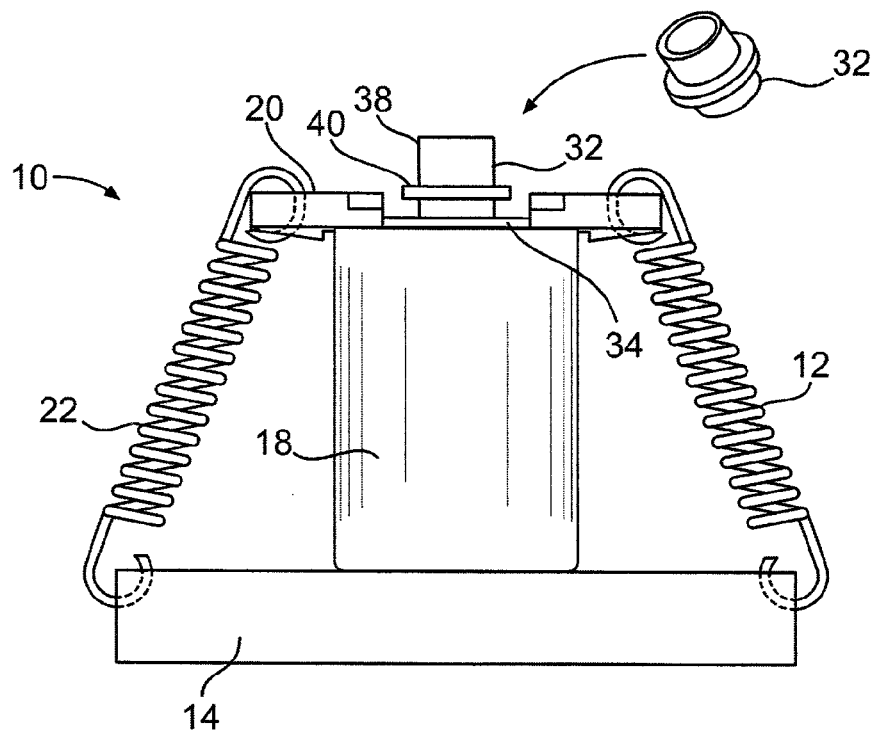
FIG. 4 is a view similar to FIG. 2 showing a mould mounted in the apparatus.
Figure 5:
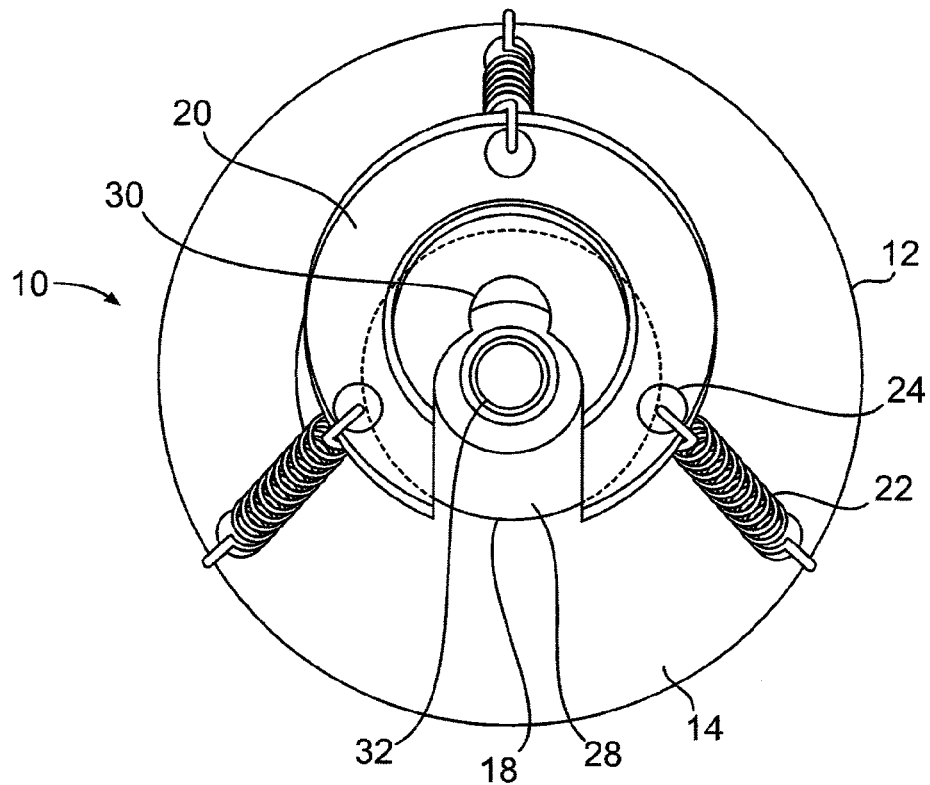
FIG. 5 is a plan view of the apparatus of FIG. 4.

Further, as can be seen in FIGS. 4 and 5 the mould 32 comprises a hollow member 38 having an outwardly extending circumferential flange 40 disposed adjacent a lower end thereof, in use. The mould 32 is open at upper and lower ends thereof and is mounted on the substrate 34, in use. The mould 32 is retained in place by engagement of the compression plate 20 with the flange 40 which presses the mould 32 onto the substrate 34.

Figure 8:
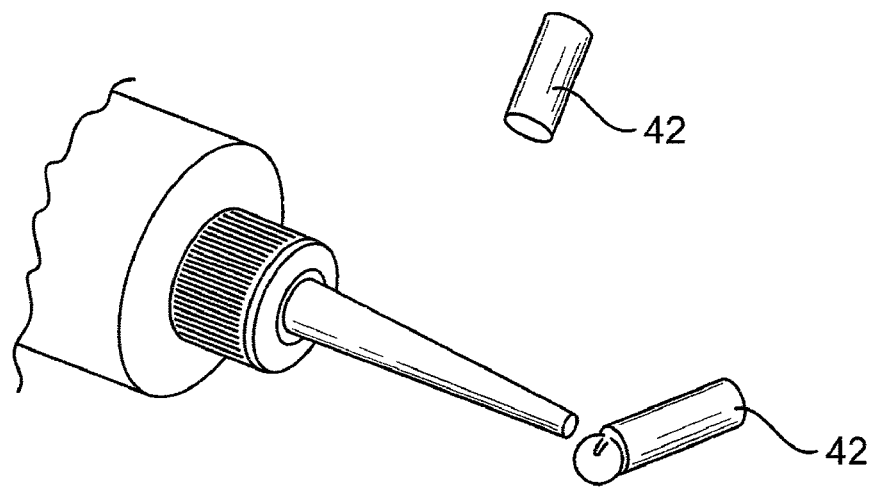
FIG. 8 shows a sample being applied.
Figure 9:
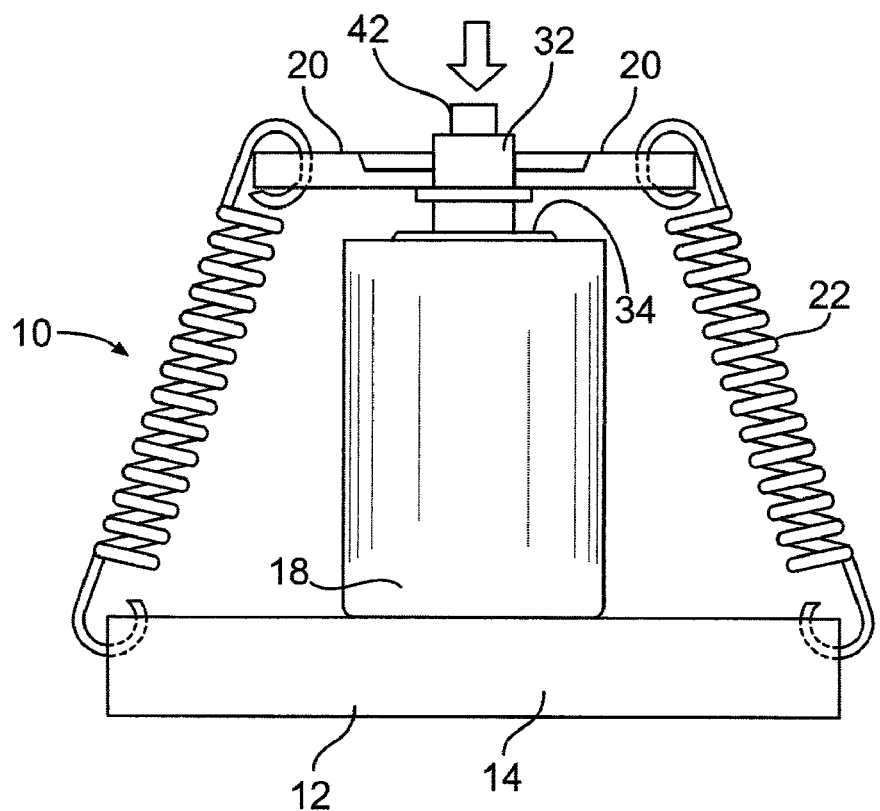
FIG. 9 shows the apparatus being prepared for testing.

Further, the apparatus 10 comprises a cylindrical pin 42, shown in FIGS. 8 and 9.

The pin 42 is dimensioned so as to fit snugly in the mould 36 such that there is only a small lateral clearance around the pin 42 when it is inserted in the mould 32 such as about 0.3 mm. The pin 42 may be made of opaque or transparent material.

In use, the support 18 is mounted on the base plate 14 within the rings 16. Thus, the substrate 34 is centrally disposed on the base plate 14 as shown in FIG. 3.

Preferably, the support 18 having the substrate 34 mounted thereon is moulded from a resin or cement material. The support 18 is treated such as by means of an abrasive material so as to expose the substrate 34 and to ensure that ends of the support 18 are substantially perpendicular to sides of the support 18.

Figure 6:
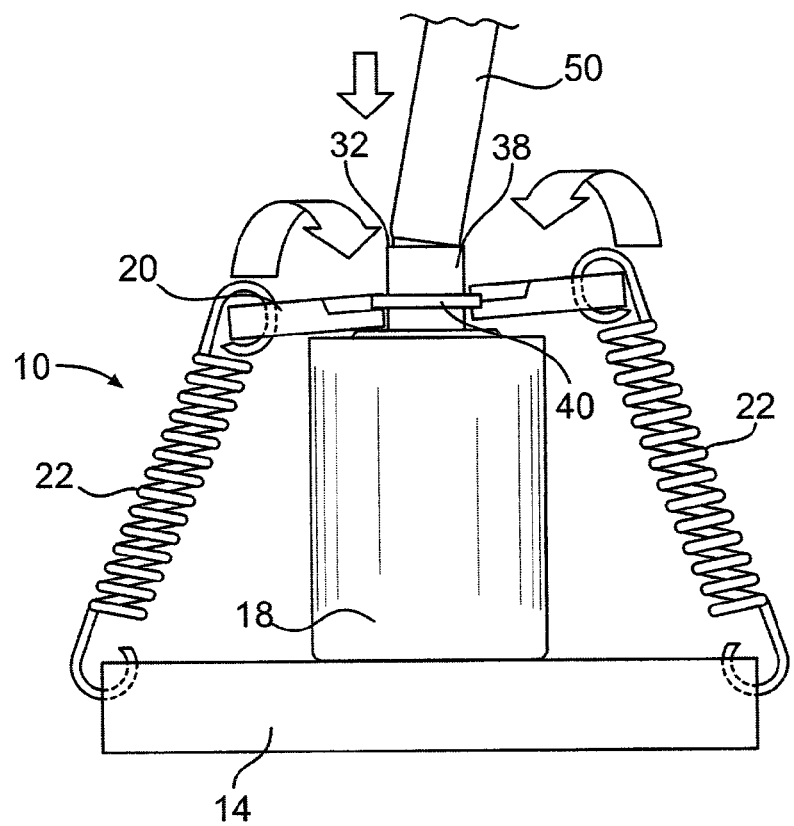
FIG. 6 is a side elevation of the apparatus of FIGS. 4 and 5 showing the mould being secured in place.
Figure 7:
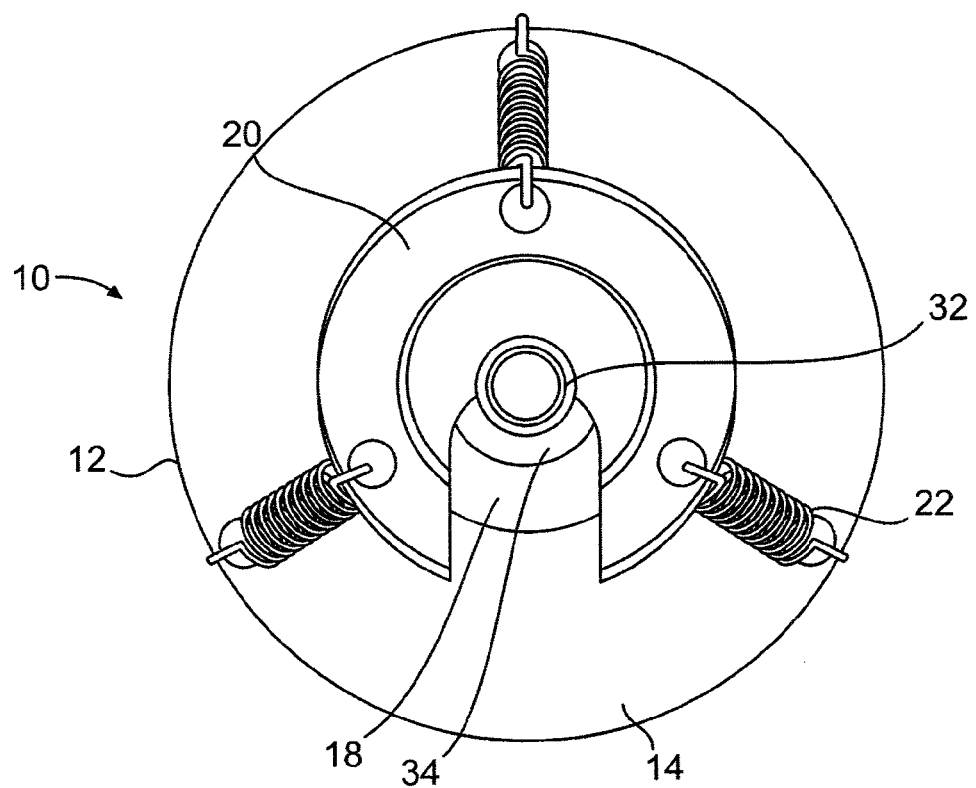
FIG. 7 is a plan view showing the mould of FIG. 6 secured in place.

Subsequently, the mould 32 is placed on the substrate 34 as shown in FIG. 4 with the compression plate 20 offset to one side. The fact that the compression plate 20 is offset enables the mould 32 to be readily placed in the desired position. Then the mould 32 is held down firmly by a suitable device 50 such as a rod or a spatula as shown in FIG. 6. The compression plate 20 is then lifted up and moved transversely so as to engage the recess 30 with the mould 32. In this position the compression plate 20 bears down on the flange 40 as shown in FIG. 7. This forces the mould 32 to engage with the surface of the substrate 34. The springs 22 ensure that the mould 32 engages perpendicularly with the substrate 34 even in the event that ends of the cylinder 18 are not level.

The system described requires no adjustment by the operator. For example, there is no requirement for adjustment of the compression plate 20 to compression in use.

Material is placed into the mould 32 or on the pin 42 depending on operator preference, as shown in FIG. 8. The pin 42 is then placed in the mould 32 with the material lowermost in the mould as shown in FIG. 9.

Figure 10:
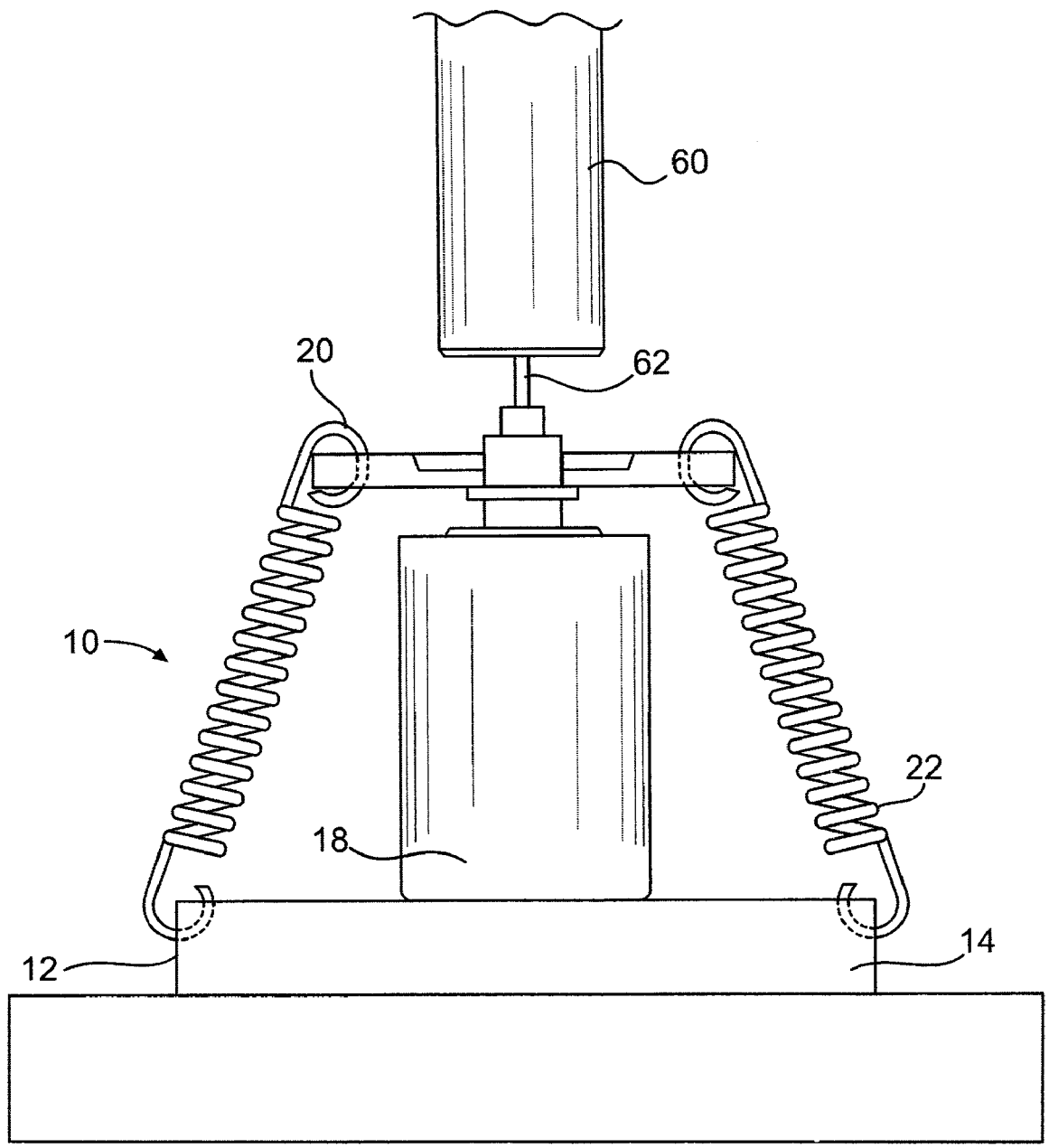
FIG. 10 shows the apparatus under test.
Figure 11:
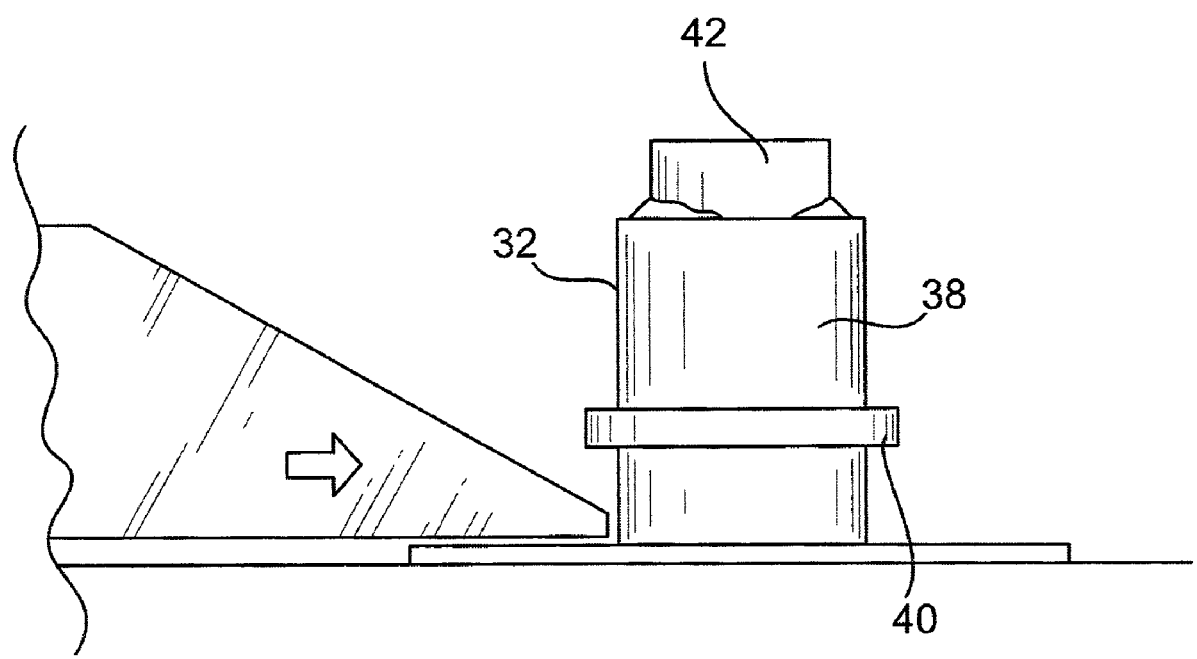
FIG. 11 shows a debonding test procedure.

The apparatus 10 is then placed in a compression weight/pressure weight apparatus 60 of known type shown in FIG. 10. The apparatus 60 is arranged to move only vertically. The apparatus 10 is placed directly under the apparatus 60. The apparatus 60 supplies pressure by means of a rod 62 on the pin 42 to initiate light finger pressure.

In another example, the mould 32 can be used without the pin 42 and without the compression weight/pressure weight apparatus 60. In this case the adhesive material is placed directly into the mould 32 and sufficient material is inserted to fill the mould 32 completely.

Subsequently the material is subjected to light cure through a transparent pin 42 (when used) or self cure at 37° C.

The compression plate 20 is then removed from the mould 32 whilst holding the base plate 14.

The substrate 34 and the mould 32 are heated together whilst remaining in contact for 24 hours at 37° C. in deionised water ensuring that the mould 32 and the pin 42 (when used) are covered.

The mould 32 is then removed from the substrate 34 by a known debonding procedure using a debonding apparatus. A shear knife or the like is used to remove the mould 32 from the substrate 34. Preferably the knife has a flat end to avoid any bending moment being translated to the mould 32.

The apparatus produces a reading of the amount of shear bond strength force of the substance in the mould which provides an accurate measure of the adhesive strength of the bond.

The present invention is envisaged to be particularly useful for determining the shear bond strength of dental cements and adhesives but it is to be understood that it is of general applicability.

It is also envisaged that the mould 32 and the pin 42 would be disposable whilst the remainder of the system could be used repeatedly on many occasions.

Modifications and variations as would be apparent to a skilled addressee are deemed to be within the scope of the present invention.

The invention claimed is:

1. An apparatus for determining the adhesive strength of materials comprising a test rig having a base plate, a compression plate resiliently mounted to said base plate, said compression plate containing a lateral aperture arranged for receiving a mould, said compression plate being spaced apart from said base plate for enabling a substrate to be located between said compression plate and said base plate, and means for urging said compression plate into engagement with said mould when said mould is mounted on said substrate.

2. An apparatus according to claim 1, wherein a support is disposed between the base plate and the compression plate, the substrate being located within the support.

3. An apparatus according to claim 1, wherein compression plate is connected to the base plate by spring means.

4. An apparatus according to claim 3, wherein the spring means takes the form of a plurality of equiangularly spaced coil springs.

5. An apparatus according to claim 1, wherein the lateral aperture in the compression plate terminates in a recess arranged to receive the mould.

6. An apparatus according to claim 1, wherein said mould comprises an open-ended hollow substantially cylindrical member having an outwardly extending external circumferential flange, said compression plate being arranged for engaging with said flange for pressing said mould onto said substrate for retaining said mould in place on said substrate.

7. An apparatus according to claim 1, wherein there is further provided a pin arranged to fit snugly in the mould.

8. A method for determining the adhesive strength of materials which comprises the steps of mounting a mould on a substrate, inserting a quantity of material to be tested into the mould, applying pressure to the mould to retain it in position on the substrate, so that the material is in contact with the substrate, and then measuring the force required to remove the mould from the substrate, wherein said mould comprises an open-ended hollow substantially cylindrical member having an outwardly extending external circumferential flange, said compression plate being arranged for engaging with said flange for pressing said mould onto said substrate for retaining said mould in place on said substrate.

9. A method according to claim 8, wherein the substrate is located within a support and the support is treated prior to use to expose the substrate.

10. A method according to claim 8, wherein the pressure is applied to the mould by means of a compression plate having a lateral aperture, the compression plate is initially offset to enable the mould to be planed, and subsequently the compression plate is engaged with the mould by means of the lateral aperture.

11. An apparatus for determining the adhesive strength of materials comprising a test rig having a base plate, a compression plate resiliently mounted to said base plate, said compression plate containing a lateral aperture arranged for receiving a mould, said compression plate being spaced apart from said base plate for enabling a substrate to be located between said compression plate and said base plate, and means for urging said compression plate into engagement with said mould when said mould is mounted on said substrate, wherein said mould comprises an open-ended hollow substantially cylindrical member having an outwardly extending external circumferential flange, said compression plate being arranged for engaging with said flange for pressing said mould onto said substrate for retaining said mould in place on said substrate.

* * * * *

UNITED STATES PATENT AND TRADEMARK OFFICE
CERTIFICATE OF CORRECTION

PATENT NO. : 8,316,702 B2
APPLICATION NO. : 12/691713
DATED : November 27, 2012
INVENTOR(S) : Joshua James Cheetham Page 1 of 1

It is certified that error appears in the above-identified patent and that said Letters Patent is hereby corrected as shown below:

Item (30) should read

(30)  Foreign Application Priority Data

Jan. 23, 2009 (AU)  ....................  2009900267

Signed and Sealed this
Twelfth Day of February, 2013

Teresa Stanek Rea
*Acting Director of the United States Patent and Trademark Office*